(12) United States Patent
Lee et al.

(10) Patent No.: US 10,646,305 B2
(45) Date of Patent: May 12, 2020

(54) DENTAL TREATMENT INSTRUMENT

(71) Applicant: B&L BIOTECH, INC., Ansan-si, Gyeonggi-do (KR)

(72) Inventors: In Whan Lee, Seoul (KR); Dong Yoon Lee, Seoul (KR); Seung Ki Baek, Seoul (KR); Gil Hwan Sung, Seoul (KR); Myun Hwan Ahn, Namyangju-si (KR); In Jeong Choi, Seoul (KR)

(73) Assignee: B&L BIOTECH, INC., Ansan-si (KR)

( * ) Notice: Subject to any disclaimer, the term of this patent is extended or adjusted under 35 U.S.C. 154(b) by 0 days.

(21) Appl. No.: 15/191,939

(22) Filed: Jun. 24, 2016

(65) Prior Publication Data

US 2017/0245957 A1 Aug. 31, 2017

(30) Foreign Application Priority Data

Feb. 26, 2016 (KR) .................. 10-2016-0023624

(51) Int. Cl.
*A61C 3/00* (2006.01)
*A61C 3/06* (2006.01)
(Continued)

(52) U.S. Cl.
CPC .............. *A61C 3/00* (2013.01); *A61C 3/06* (2013.01); *A61B 1/247* (2013.01); *A61B 2017/00464* (2013.01); *A61C 3/08* (2013.01)

(58) Field of Classification Search
CPC .... A61C 3/00; A61C 3/06; A61C 3/08; A61C 1/088; A61B 1/247; A61B 2017/00464
(Continued)

(56) References Cited

U.S. PATENT DOCUMENTS 5,741,084 A * 4/1998 Del Rio ............. A61B 17/1633
285/361
5,816,806 A 10/1998 Herbst et al.
(Continued)

FOREIGN PATENT DOCUMENTS

| JP | 8-322852 A | 12/1996 |
| JP | 2010-35688 A | 2/2010 |
| KR | 10-2012-0127314 A | 11/2012 |

OTHER PUBLICATIONS

Korean Office Action for the corresponding Korean Patent Application No. 10-2016-0023624 dated Jan. 24, 2017.
(Continued)

*Primary Examiner* — Heidi M Eide
*Assistant Examiner* — Drew S Folgmann
(74) *Attorney, Agent, or Firm* — Sughrue Mion, PLLC

(57) ABSTRACT

A dental treatment instrument includes a bridge unit, and a first tip and a second tip unit each configured to be replaceable with respect to the bridge unit, where the bridge unit includes a first lengthwise groove formed in a lengthwise direction at one end of the bridge unit, a first circumferential groove extending from the first lengthwise groove in a first circumferential direction, a second lengthwise groove formed in the lengthwise direction at the other end of the bridge unit, and a second circumferential groove extending from the second lengthwise groove in a second circumferential direction different from the first circumferential direction, and the first tip unit includes a first coupling protrusion extending in a direction vertical to the lengthwise direction of the bridge unit, and the second tip unit includes a second coupling protrusion extending in a direction vertical to the lengthwise direction of the bridge unit.

5 Claims, 4 Drawing Sheets

(51) Int. Cl.
*A61B 1/247* (2006.01)
*A61C 3/08* (2006.01)
*A61B 17/00* (2006.01)

(58) Field of Classification Search
USPC .......................................................... 433/126
See application file for complete search history.

(56) References Cited

U.S. PATENT DOCUMENTS

| | | |
|---|---|---|
| 6,322,362 B1 | 11/2001 | Holms |
| 2002/0162180 A1 | 11/2002 | Blaustein et al. |
| 2004/0038176 A1* | 2/2004 | Hallows .................. A61C 3/00 433/141 |
| 2004/0166474 A1 | 8/2004 | Gugel et al. |
| 2006/0084032 A1* | 4/2006 | Tipton .................... A61C 3/00 433/141 |
| 2011/0223559 A1* | 9/2011 | Jamnia ................... A61C 3/00 433/143 |
| 2015/0359950 A1 | 12/2015 | Salehi |
| 2016/0038348 A1 | 2/2016 | Booth et al. |

OTHER PUBLICATIONS

Communication dated Jan. 30, 2018, issued by Japanese Patent Office in counterpart Japanese Patent Application No. 2017-033511.
Communication dated Aug. 22, 2017 from the Australian Patent Office in corresponding Australian Patent Application No. 2017200161.

* cited by examiner

DENTAL TREATMENT INSTRUMENT

CROSS-REFERENCE TO RELATED APPLICATION

This application claims the priority benefit of Korean Patent Application No. 10-2016-0023624, filed on Feb. 26, 2016, in the Korean Intellectual Property Office, the disclosure of which is incorporated herein by reference.

BACKGROUND

1. Technical Field

At least one example embodiment relates to a dental surgical instrument, and more particularly, to a dental surgical instrument that may facilitate replacement into various types of tip units, thereby improving an operational convenience.

2. Related Art

A decayed tooth, i.e., dental caries, refers to a state in which an ivory white, transparent, and hard material, i.e., a dental enamel that protects a dentin of a tooth is damaged by acid occurring while sugar, starchy, etc., being dissolved by bacteria living in the mouth. Here, the dentin of the tooth serves to cover the surface of a head portion of the tooth.

In the case of treating the decayed tooth, a liner for removing a portion of the tooth is formed using a dental hand piece and one of amalgam, photopolymer resin, self-polymeric resin, glass ionomer, gold inlay, resin inlay, zirconium, etc., may be selected as a filling material and fill in the liner. Here, the treatment of the decayed tooth may be completed by hardening and smoothly polishing the filling material filled in the liner.

Various types of dental tips, such as a plugger for stomping and thereby filling the filling material, a burnisher for smoothly polishing the filling material, a carver for forming the filling material to fit for a shape of the tooth, a mirror for verifying an inside of the mouth, a file for removing the nerve, and the like, are employed during a series of dental treatment process.

The various types of dental tips may be formed based on various types of standards and shapes, and may be selectively utilized by a user, for example, a dentist, a relevant curer, etc. However, in the case of a dental tip according to the related art, tips based on different standards may be provided at both ends of a single treatment instrument in a handle shape. Thus, a plurality of tips is to be provided for a dental treatment operation of the user. In addition, the user needs to replace a tip with another suitable tip and then grip the treatment instrument. Accordingly, a variety of researches are being conducted on a dental treatment instrument to improve the treatment convenience of a user, for example, a dentist, a relevant curer, etc.

SUMMARY

Example embodiments provide a dental treatment instrument that may simply and easily replace a tip unit, thereby improving the use convenience of a user, for example, a dentist, a relevant curer, and the like.

According to an aspect of example embodiments, there is provided a dental treatment instrument including a bridge unit configured to be gripped by a user; a plurality of tip units configured to be replaceable with respect to the bridge unit; and a coupling unit configured to selectively couple the tip unit with the bridge unit. The coupling unit is configured to couple the tip unit with the bridge unit by inserting and thereby rotating a portion of the tip unit relative to the bridge unit.

Each of the plurality of tip units may include a plurality of tips in different shapes, respectively.

The coupling unit may include a coupling groove provided to one of the bridge unit and the tip unit; and a coupling protrusion provided to the other one of the bridge unit and the tip unit, and configured to insert into the coupling groove.

The coupling groove may include a first groove formed in an insertion direction of the tip unit relative to the bridge unit; and a second groove configured to extend from the first groove toward an orthogonal direction and to guide the coupling protrusion not to move in the insertion direction.

The coupling groove may include a first groove formed in a lengthwise direction at each of both ends of the bridge unit; and a second groove formed in a circumferential direction of the bridge unit orthogonal to the first groove, and the coupling groove may be provided in a reverse "L" shape.

The coupling groove may be provided to the bridge unit, and the coupling protrusion may be provided to the tip unit.

The coupling groove may be provided to a bridge bracket that is disposed inside the bridge unit, and the coupling protrusion may be provided to a tip bracket that is disposed inside the tip unit.

The coupling unit may include an O-ring provided between the bridge unit and the tip unit and configured to seal a space between the bridge unit and the tip unit.

According to another aspect of example embodiments, there is provided a dental treatment instrument including a bridge unit configured to be gripped by a user; a plurality of tip units each including a plurality of tip portions having a plurality of tips in different shapes, respectively; and a coupling unit configured to couple at least one of the plurality of tip portions with the bridge unit. The coupling unit is configured to guide mutual coupling between the tip portion and the bridge unit by inserting and thereby rotating the tip portion in a lengthwise direction of the plurality of tip portions relative to the bridge unit.

The coupling unit may include a coupling groove provided to one of the bridge unit and the tip unit; and a coupling protrusion provided to the other one of the bridge unit and the tip unit, and configured to insert into the coupling groove.

The coupling groove may include a first groove formed in an insertion direction of the tip unit relative to the bridge unit; and a second groove configured to extend from the first groove toward an orthogonal direction and to guide the coupling protrusion not to move in the insertion direction.

The coupling groove may be provided to the bridge unit, and the coupling protrusion is provided to the tip unit. The coupling groove may include a first groove formed in a lengthwise direction at each of both ends of the bridge unit; and a second groove formed in a circumferential direction of the bridge unit orthogonal to the first groove, and the coupling groove may be provided in a reverse "L" shape.

The coupling unit may include an O-ring provided between the bridge unit and the tip unit and configured to seal a space between the bridge unit and the tip unit.

According to example embodiments, it is possible to provide a desired combination suitable for a surgical purpose of a user, for example, a dentist, a relevant curer, etc., by selectively coupling one of a plurality of tip units with a bridge unit.

Also, a replacement operation may be easily performed by inserting the tip unit relative to the bridge unit and by fixing a clamping force between the tip unit and the bridge unit through a rotation operation at a desired angle.

Also, the convenience of the user may be enhanced by replacing a desired tip through a simple replacement operation.

According to an aspect of example embodiments, there is provided a dental treatment instrument including a first tip unit including a first tip cover and a first tip bracket element, the first tip cover being configured to support a first tip, a bridge unit configured to be gripped by a user and including a bridge cover in a shape of a hollow cylinder and a bridge bracket, and a second tip unit including a second tip cover and a second tip bracket element, the second tip cover being configured to support a second tip, and each of the first tip unit and the second tip unit is configured to be replaceable with respect to the bridge unit, the bridge bracket is in a shape of a hollow cylinder having an inner circumferential surface and an outer circumferential surface, includes a first end and a second end and extends from the first end to the second end, and the bridge bracket includes a first lengthwise groove formed along a first lengthwise direction of the bridge bracket from the first end of the bridge bracket toward the second end of the bridge bracket, a first circumferential groove extending from the first lengthwise groove and formed along a first circumferential direction of the bridge bracket, a second lengthwise groove formed along a second lengthwise direction of the bridge bracket from the second end of the bridge bracket toward the first end of the bridge bracket, the first lengthwise direction being opposite to the second lengthwise direction, and a second circumferential groove extending from the second lengthwise groove and formed along a second circumferential direction of the bridge bracket different from the first circumferential direction, and each of the first lengthwise groove, the first circumferential groove, the second lengthwise groove, and the second circumferential groove is a groove passing though from a portion of the inner circumferential surface to a portion of the outer circumferential surface, and the first tip bracket element of the first tip unit includes a first tip bracket, a first tip fixing step and a first coupling end portion, and the first tip bracket extends in the second lengthwise direction from the first tip fixing step, and the first coupling end portion extends in the first lengthwise direction from the first tip fixing step and is in a shape of a cylinder having a first outer circumferential surface, and a dimeter of the first tip fixing step is larger than each of a diameter of the first tip bracket and a dimeter of the first coupling end portion, and the second tip bracket element of the second tip unit includes a second tip bracket, a second tip fixing step and a second coupling end portion, and the second tip bracket extends in the first lengthwise direction from the second tip fixing step, and the second coupling end portion extends in the second lengthwise direction from the second tip fixing step and is in a shape of a cylinder having a second outer circumferential surface, and a dimeter of the second tip fixing step is larger than each of a diameter of the second tip bracket and a dimeter of the second coupling end portion, and the first tip bracket of the first tip bracket element is provided inside the first tip cover of the first tip unit, and the second tip bracket of the second tip bracket element is provided inside the second tip cover of the second tip unit, and the first tip bracket element further includes a first coupling protrusion protruding from the first outer circumferential surface of the first coupling end portion in a radial direction vertical to the first lengthwise direction, and the second tip bracket element further includes a second coupling protrusion protruding from the second outer circumferential surface of the second coupling end portion in a radial direction vertical to the second lengthwise direction, and the first coupling protrusion of the first tip bracket element is configured to couple with the first circumferential groove of the bridge bracket by inserting the first coupling protrusion along the first lengthwise groove in the first lengthwise direction and rotating the first coupling protrusion in the first circumferential direction, and the second coupling protrusion of the second tip bracket element is configured to couple with the second circumferential groove of the bridge bracket by inserting the second coupling protrusion along the second lengthwise groove in the second lengthwise direction and rotating the second coupling protrusion in the second circumferential direction, and the bridge bracket, at least a part of the first tip fixing step of the first tip bracket element, and at least a part of the second tip fixing step of the second tip bracket element are provided inside the bridge cover, and the first tip cover of the first tip unit and the bridge cover are connected to each other at a first portion of the dental treatment instrument and have a same external diameter at the first portion of the dental treatment instrument, and the second tip cover of the second tip unit and the bridge cover are connected to each other at a second portion of the dental treatment instrument and have a same external diameter at the second portion of the dental treatment instrument.

According to another aspect of example embodiments, there is provided a dental treatment instrument including a first tip unit including a first tip in a first shape, a first tip cover and a first tip bracket element, the first tip cover being configured to support the first tip, a bridge unit configured to be gripped by a user, and a second tip unit including a second tip in a second shape, a second tip cover and a second tip bracket element, the second tip cover being configured to support the second tip, and the second shape is different from the first shape, the bridge unit includes a bridge cover in a shape of a hollow cylinder and a bridge bracket inside the bridge cover, the bridge bracket is in a shape of a hollow cylinder having an inner circumferential surface and an outer circumferential surface, includes a first end and a second end and extends from the first end to the second end, and the bridge bracket includes a first lengthwise groove formed along a first lengthwise direction of the bridge bracket from the first end of the bridge bracket toward the second end of the bridge bracket, a first circumferential groove extending from the first lengthwise groove and formed along a first circumferential direction of the bridge bracket, a second lengthwise groove formed along a second lengthwise direction of the bridge bracket from the second end of the bridge bracket toward the first end of the bridge bracket, the first lengthwise direction being opposite to the second lengthwise direction, and a second circumferential groove extending from the second lengthwise groove and formed along a second circumferential direction of the bridge bracket different from the first circumferential direction, and each of the first lengthwise groove, the first circumferential groove, the second lengthwise groove, and the second circumferential groove is a groove passing though from a portion of the inner circumferential surface to a portion of the outer circumferential surface, and the first tip bracket element of the first tip unit includes a first tip bracket, a first tip fixing step and a first coupling end portion, and the first tip bracket extends in the second lengthwise direction from the first tip fixing step, and the first coupling end portion extends in the first lengthwise direction from the first tip fixing step and is in a shape of a cylinder having a first outer circumferential surface, and a dimeter of the first tip fixing step is larger than each of a diameter of the first tip bracket and a dimeter of the first coupling end portion, and the second tip bracket element of the second tip unit includes a second tip bracket, a second tip fixing step and a second coupling end portion, and the second tip bracket extends in the first lengthwise direction from the second tip fixing step, and the second coupling end portion extends in the second lengthwise direction from the second tip fixing step and is in a shape of a cylinder having a second outer circumferential surface, and a dimeter of the second tip fixing step is larger than each of a diameter of the second tip bracket and a dimeter of the second coupling end portion, and the first tip bracket of the first tip bracket element is provided inside the first tip cover of the first tip unit, and the second tip bracket of the second tip bracket element is provided inside the second tip cover of the second tip unit, and the first tip bracket element further includes a first coupling protrusion protruding from the first outer circumferential surface of the first coupling end portion in a radial direction vertical to the first lengthwise direction of the bridge bracket, and the second tip bracket element further includes a second coupling protrusion protruding from the second outer circumferential surface of the second coupling end portion in a radial direction vertical to the second lengthwise direction of the bridge bracket, and the first coupling protrusion of the first tip bracket element is configured to couple with the first circumferential groove of the bridge bracket, and the second coupling protrusion of the second tip bracket element is configured to couple with the second circumferential groove of the bridge bracket, and the bridge bracket, at least a part of the first tip fixing step of the first tip bracket element, and at least a part of the second tip fixing step of the second tip bracket element are provided inside the bridge cover, and the first tip cover of the first tip unit and the bridge cover are connected to each other at a first portion of the dental treatment instrument and have a same external diameter at the first portion of the dental treatment instrument, and the second tip cover of the second tip unit and the bridge cover are connected to each other at a second portion of the dental treatment instrument and have a same external diameter at the second portion of the dental treatment instrument.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION OF THE INVENTION

Figure 1:
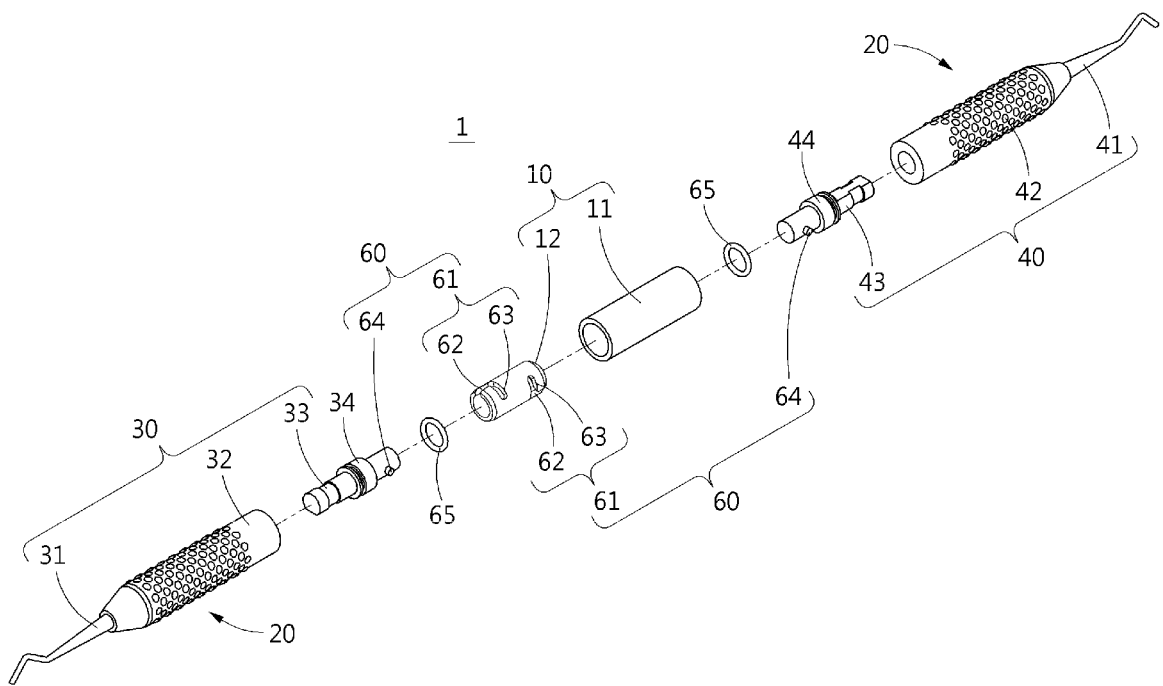
FIG. 1 is a perspective view illustrating a dental treatment instrument according to at least one example embodiment.

Hereinafter, example embodiments will be described with reference to the accompanying drawings. Herein, thicknesses of lines, sizes of constituent elements, etc., illustrated in the drawings, may be exaggerated for clarity and convenience of description. Further, terms described in the following are ones defined based on functions in the present disclosure and thus, may vary based on the intent of a user or an operator, or custom. Accordingly, the definition of such terms should be made based on the overall description disclosed in the present specification.

Although the terms "first," "second," "third," etc., may be used herein to describe various elements, components, regions, layers, and/or sections, these elements, components, regions, layers, and/or sections, should not be limited by these terms. These terms are only used to distinguish one element, component, region, layer, or section, from another region, layer, or section. Thus, a first element, component, region, layer, or section, discussed below may be termed a second element, component, region, layer, or section, without departing from the scope of this disclosure.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

Hereinafter, example embodiments will be described with reference to the accompanying drawings.

Figure 2:
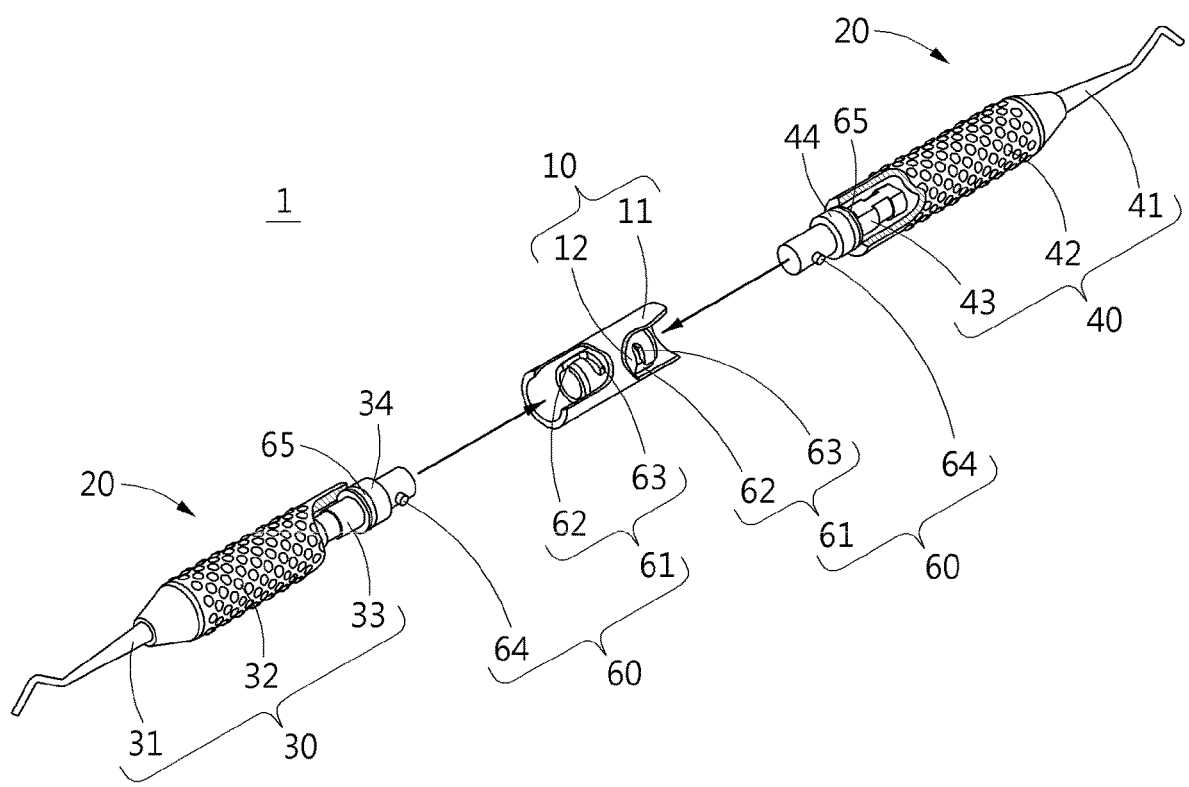
FIGS. 2 and 3 are perspective views illustrating an operation of coupling a first tip portion and a second tip portion with a bridge unit of FIG. 1.
Figure 3:
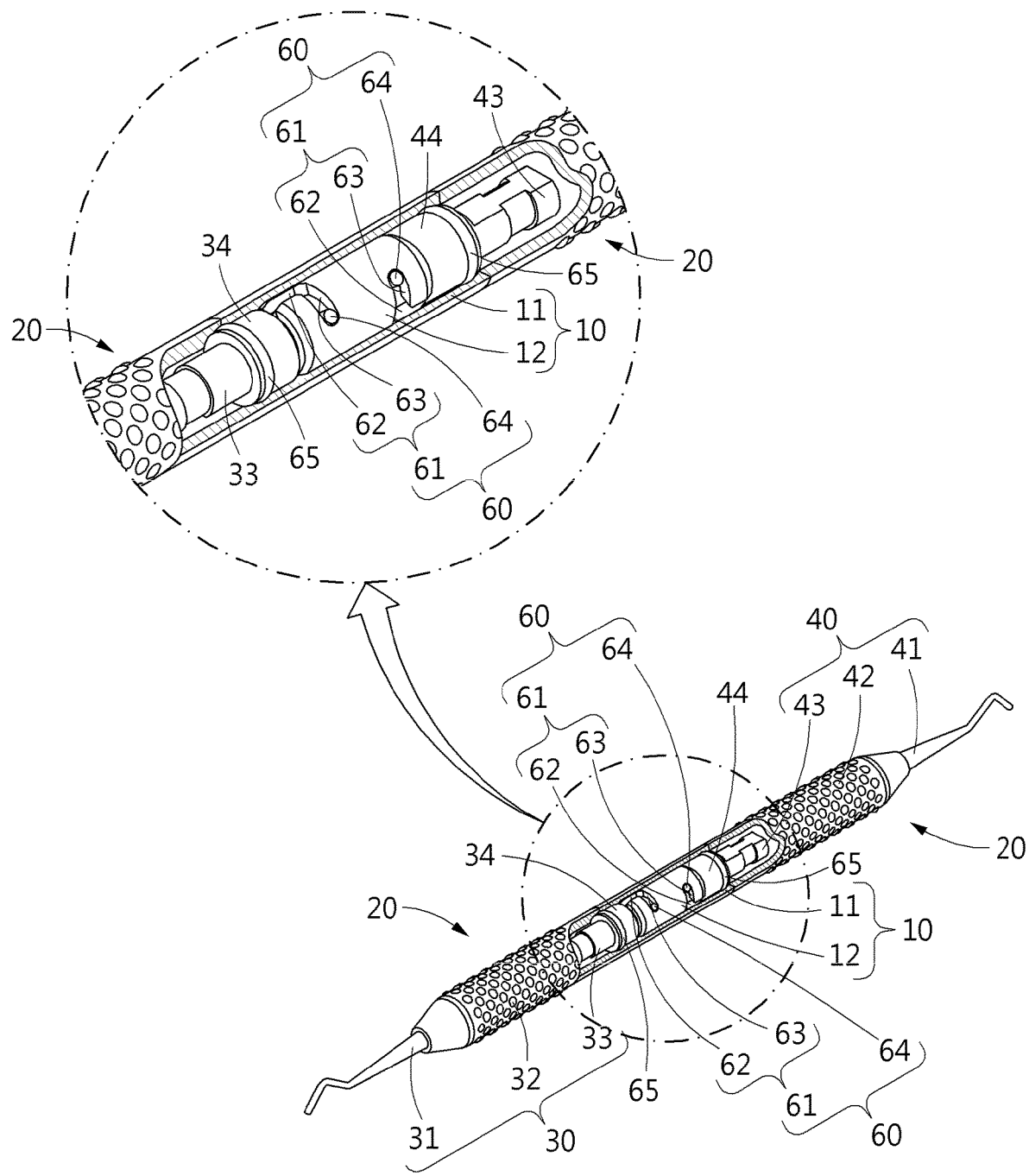
Figure 4:
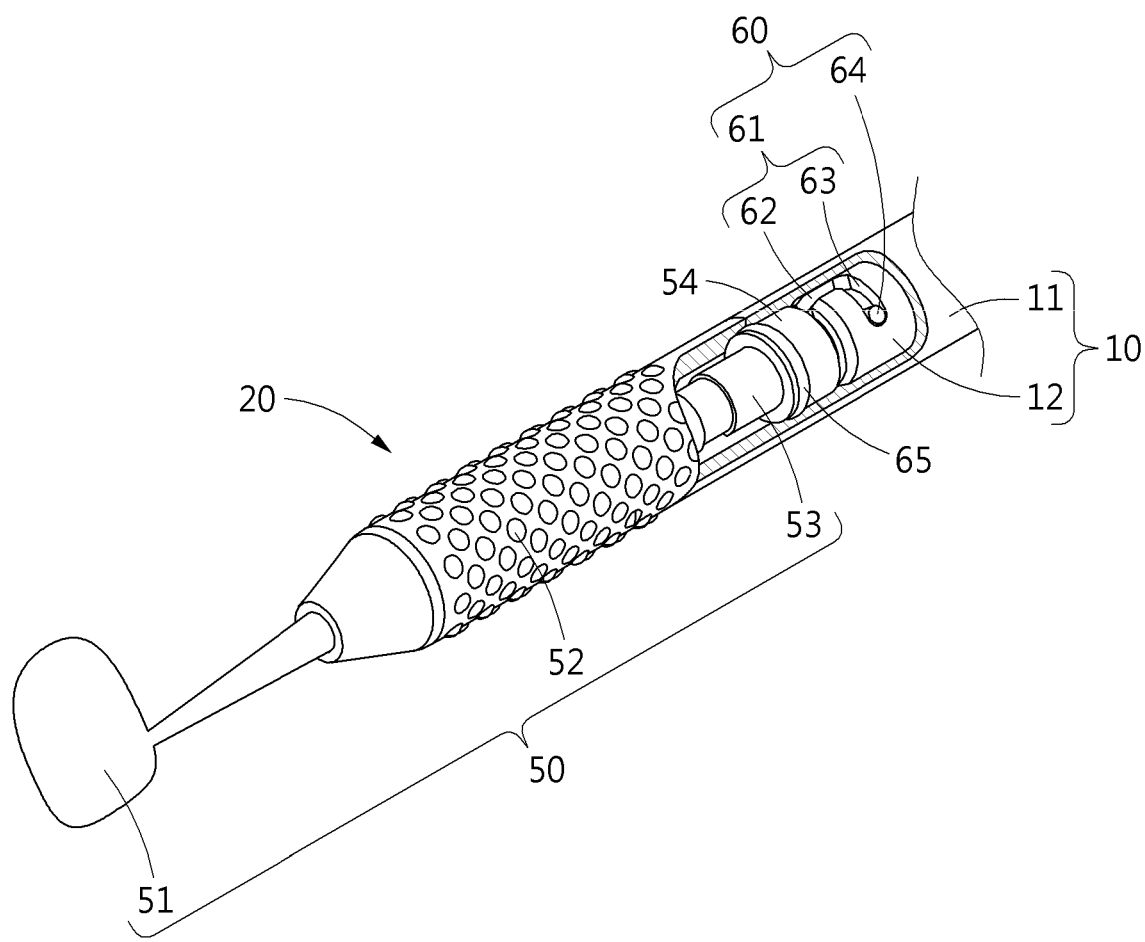
FIG. 4 is a perspective view illustrating a state in which a third tip is coupled with the bridge unit of FIG. 1.

FIG. 1 is a perspective view illustrating a dental treatment instrument according to at least one example embodiment, FIGS. 2 and 3 are perspective views illustrating an operation of coupling a first tip portion and a second tip portion with a bridge unit of FIG. 1, and FIG. 4 is a perspective view illustrating a state in which a third tip is coupled with the bridge unit of FIG. 1.

Referring to FIG. 1, a dental treatment instrument 1 includes a bridge unit 10, a tip unit 20, and a coupling unit 60.

The bridge unit 10 is configured to be gripped by a user, for example, a dentist, a relevant curer, and the like, and is a body of the dental treatment instrument 1. The bridge unit 10 includes a bridge cover 11 in a hollow cylindrical shape and a hollow bridge bracket 12 provided inside the bridge cover 11. The bridge bracket 12 may be formed using a stainless steel material having rigidity. The tip unit 20 may be installed at each of both ends of the bridge unit 10.

A plurality of tip units 20 may be provided to be replaceable with respect to the bridge unit 10. Hereinafter, for clarity of description, the tip unit 20 may include a plurality of tip portions 30, 40, and 50 having a plurality of tips 31, 41, and 51 in different shapes, respectively. That is, the tip unit 20 may include first and second tip portions 30 and 40 as shown in FIGS. 1 through 3 and a third tip portion 50 as shown in FIG. 4.

The first tip portion 30 includes a first tip 31 having a first shape, a first tip cover 32 configured to support the first tip 31 and to be gripped by the user, and a first tip bracket 33 provided inside the first tip cover 32.

For example, the first tip 31 may be a plugger used for treating a decayed tooth. The first tip cover 32 may be provided in a hollow cylindrical shape into which the first tip bracket 33 is inserted. An unevenness for helping a gripping power of the user may be provided on the outer circumferential surface of the first tip cover 32. Here, the first tip cover 32 may be connected to the bridge cover 11. To achieve esthetics and well-grip, the first tip cover 32 and the bridge cover 11 may have the same external diameter at an end portion at which the first tip cover 32 and the bridge cover 11 are connected to each other.

The second tip portion 40 includes a second tip 41 having a second shape different from the first shape of the first tip 31, a second tip cover 42 configured to support the second tip 41 and to be gripped by the user, and a second tip bracket 43 provided inside the second tip cover 42. Here, aside from a shape of the second tip 41, the second tip cover 42 and the second tip bracket 43 may be configured to be same as those of the first tip portion 30. Thus, a further description will be omitted. For example, the second tip 41 of the second tip portion 40 may be a burnisher.

Referring to FIG. 4, the third tip portion 50 includes a third tip 51, for example, a mirror, for verifying inside of the mouth, a third tip cover 52 configured to support the third tip 51 and to be gripped by the user, and a third tip bracket 53 provided inside the third tip cover 52. Here, aside from a shape of the third tip 51, the third tip cover 52 and the third tip bracket 53 of the third tip portion 50 may be configured to be same as those of the first and second tip portions 30 and 40. Thus, a further description will be omitted.

Although FIGS. 1 through 4 illustrate the first tip 31, the second tip 41, and the third tip 51 as the plugger, the burnisher, and the mirror, respectively, they are only examples and the example embodiments are not limited thereto. Thus, various types of dental treatment tips, such as a file, a clamp, and the like, may be applicable.

The first tip bracket 33, the second tip bracket 43, and the third tip bracket 53 may have an external diameter less than that of the bridge bracket 12 to be partially inserted into the hollow bridge bracket 12.

The coupling unit 60 may selectively couple the tip unit 20 with the bridge unit 10. The coupling unit 60 includes a coupling groove 61 provided to one of the bridge unit 10 and the tip unit 20 and a coupling protrusion 64 provided to the other one of the bridge unit 10 and the tip unit 20, and configured to insert into the coupling groove 61. According to example embodiments, the coupling groove 61 may be provided to the bridge unit 10 and the coupling protrusion 64 may be provided to the tip unit 20.

In detail, the coupling groove 61 may be provided to the bridge bracket 12 that is disposed inside the bridge cover 11, and the coupling protrusion 64 may be provided to each of the tip brackets 33, 43, and 53 of the tip unit 20. Here, the coupling groove 61 may be provided at both ends of the bridge bracket 12 as a single pair. The coupling protrusion 64 may be provided to each of the tip portions 30, 40, and 50.

The coupling groove 61 includes a first groove 62 formed in an insertion direction of the tip unit 20 relative to the bridge unit 10, that is, a lengthwise direction of the bridge unit 10 and a second groove 63 extend from the first groove 62 toward an orthogonal direction to the first groove 62, that is, a circumferential direction of the bridge unit 10 and to guide the coupling protrusion 64 not to move in the insertion direction. The first groove 62 and the second groove 63 of the coupling groove 61 are connected to each other in a reverse "L" shape.

The coupling protrusion 64 may be provided to each of the first through third tip brackets 33, 43, and 53 that are provided to the first through third tip portions 30, 40, and 50, respectively. In detail, the coupling protrusion 64 may protrude from each of coupling ends of the first through the third tip brackets 33, 43, and 53 that are coupled at both ends of the bridge bracket 12. The coupling protrusion 64 may guide the tip unit 20 to couple with the bridge unit 10 by sequentially passing through the first groove 62 and the second groove 63. Inversely, the coupling protrusion 640 may guide the tip unit 20 to be separate from the bridge unit 10 by sequentially passing through the second groove 63 and the first groove 62.

Meanwhile, the coupling unit 60 includes an O-ring 65 provided between the bridge unit 10 and the tip unit 20 to seal a space between the bridge unit 10 and the tip unit 20. An O-ring 65 may be provided as a single pair to seal a space between both ends of the bridge bracket 12 of the bridge unit 10 and the tip unit 20. In detail, the O-rings 65 may be disposed between ends of the bridge bracket 12 and the plurality of tip brackets 33, 43, and 53.

In this instance, the first through third tip brackets 33, 43, and 53 have an external diameter less than that of the bridge bracket 12. Thus, each of the first through third tip brackets 33, 43, and 53 each to which the coupling protrusion 64 is provided may be inserted into the bridge bracket 12 at a predetermined (or, alternatively, desired) depth along the coupling groove 61. Also, first through third tip fixing steps 34, 44, and 54 may protrude from the first through third tip brackets 33, 43, and 53, respectively, to correspond to the external diameter of the bridge bracket 12.

Through the configuration as above, in a state in which the coupling protrusion 64 provided to each of the first through third tip brackets 33, 43, and 53 is inserted and received in the bridge bracket 12 along the coupling groove 61, the O-rings 65 may be closely attached to the first through third tip fixing steps 34, 44, and 54 that are provided to the first through third tip brackets 33, 43, and 53, respectively, to thereby seal a space from the bridge unit 10.

Hereinafter, an assembly operation of the dental treatment instrument 1 according to example embodiment will be described with reference to FIGS. 2 through 4.

Referring to FIG. 2, the first tip portion 30 and the second tip portion 40 are inserted into the bridge unit 10 in the lengthwise direction. Here, the coupling protrusion 64 provided to each of the first tip bracket 33 of the first tip portion 30 and the second tip bracket 43 of the second tip portion 40 is inserted along the first groove 62 of the coupling groove 61 provided at each of both ends of the bridge bracket 12 of the bridge unit 10.

Referring to FIG. 3, the first tip portion 30 and the second tip portion 40 rotate at preset angles in a direction indicated by arrow indicators, and the coupling protrusion 64 provided to each of the first and second tip brackets 33 and 43 moves along the second groove 63 of the coupling groove 61 provided at each of both ends of the bridge bracket 12. Accordingly, the first tip portion 30 and the second tip portion 40 may be coupled relative to the bridge unit 10, and may be fixed without being moved in the insertion direction. Here, the O-ring 65 may be disposed between the mutually coupled first and second tip portions 30 and 40 and bridge unit 10 to seal a space therebetween.

If a user, for example, a dentist, a relevant curer, etc., desires to use another tip instead of using the first tip portion 30 and/or the second tip portion 40, the user may separate one of the first tip portion 30 and the second tip portion 40 coupled with the bridge unit 10 from the bridge unit 10. In detail, if the user desires to replace the first tip portion 30 with the third tip portion 50 of FIG. 4, the user may rotate the first tip portion 30 in a direction opposite to the direction indicated by the arrow indicator of FIG. 3 and may move the coupling protrusion 64 along the second groove 63. The user may move the first tip portion 30 in a direction opposite to the direction, for example, the insertion direction, indicated by the arrow indicator of FIG. 2, may move the coupling protrusion 64 along the first groove 62, and may release a clamping force between the bridge unit 10 and the first tip portion 30.

Once the first tip portion 30 is removed from the bridge unit 10, the user may couple the third tip portion 50 with the bridge unit 10 by allowing the coupling protrusion 64 of the third tip portion 50 to sequentially pass through the first and second grooves 62 and 63 of the coupling groove 61 provided to the bridge unit 10. Here, the O-ring 65 may be provided between the mutually coupled bridge unit 10 and third tip portion 50 to thereby seal a space therebetween.

According to example embodiments, it is possible to easily perform a replacement operation by inserting a desired tip portion among the first through third tip portions 30, 40, and 50 having the first through third tips 31, 41, and 51 in different shapes, respectively, relative to the bridge unit 10 and then rotating the inserted tip portion at a predetermined (or, alternatively, preset) angle.

Although a few example embodiments have been shown and described, the present disclosure is not limited to the described embodiments. Instead, it would be appreciated by those skilled in the art that changes may be made to these embodiments without departing from the principles and spirit of the disclosure, the scope of which is defined by the claims and their equivalents.

What is claimed is:

1. A dental treatment instrument comprising:
a first tip unit including a first tip cover and a first tip bracket element coupled to the first tip cover, wherein the first tip cover is configured to support a first tip and the first tip bracket element is detachable from the first tip cover;
a bridge unit configured to be gripped by a user and including a bridge cover in a shape of a hollow cylinder and a bridge bracket; and
a second tip unit including a second tip cover and a second tip bracket element coupled to the second tip cover, wherein the second tip cover is configured to support a second tip and the second tip bracket element is detachable from the second tip cover;
wherein each of the first tip unit and the second tip unit is configured to be replaceable with respect to the bridge unit,
wherein the bridge cover includes a first end and a second end and extends from the first end to the second end,
wherein the bridge bracket is in a shape of a hollow cylinder having an inner circumferential surface and an outer circumferential surface, includes a first end and a second end and extends from the first end of the bridge bracket to the second end of the bridge bracket,
where a length of the bridge cover from the first end of the bridge cover to the second end of the bridge cover is greater than a length of the bridge bracket from the first end of the bridge bracket to the second end of the bridge bracket,
wherein the bridge bracket includes:
a first lengthwise groove formed along a first lengthwise direction of the bridge bracket from the first end of the bridge bracket toward the second end of the bridge bracket,
a first circumferential groove extending from the first lengthwise groove and formed along a first circumferential direction of the bridge bracket,
a second lengthwise groove formed along a second lengthwise direction of the bridge bracket from the second end of the bridge bracket toward the first end of the bridge bracket, the first lengthwise direction being opposite to the second lengthwise direction, and
a second circumferential groove extending from the second lengthwise groove and formed along a second circumferential direction of the bridge bracket different from the first circumferential direction,
wherein each of the first lengthwise groove, the first circumferential groove, the second lengthwise groove, and the second circumferential groove is a groove passing through from a portion of the inner circumferential surface to a portion of the outer circumferential surface,
wherein the first tip bracket element of the first tip unit includes a first tip bracket, a first tip fixing step and a first coupling end portion, and the first tip bracket extends in the second lengthwise direction from the first tip fixing step, and the first coupling end portion extends in the first lengthwise direction from the first tip fixing step and is in a shape of a cylinder having a first outer circumferential surface, and a dimeter of the first tip fixing step is larger than each of a diameter of the first tip bracket and a dimeter of the first coupling end portion,
wherein the second tip bracket element of the second tip unit includes a second tip bracket, a second tip fixing step and a second coupling end portion, and the second tip bracket extends in the first lengthwise direction from the second tip fixing step, and the second coupling end portion extends in the second lengthwise direction from the second tip fixing step and is in a shape of a cylinder having a second outer circumferential surface, and a dimeter of the second tip fixing step is larger than each of a diameter of the second tip bracket and a dimeter of the second coupling end portion,
wherein the first tip bracket of the first tip bracket element is provided inside the first tip cover of the first tip unit and coupled to the first tip cover of the first tip unit, and the second tip bracket of the second tip bracket element is provided inside the second tip cover of the second tip unit and coupled to the second tip cover of the second tip unit,
wherein the first tip bracket element further includes a first coupling protrusion protruding from the first outer circumferential surface of the first coupling end portion in a radial direction vertical to the first lengthwise direction, and the second tip bracket element further includes a second coupling protrusion protruding from the second outer circumferential surface of the second coupling end portion in a radial direction vertical to the second lengthwise direction,
wherein the first coupling protrusion of the first tip bracket element is configured to couple with the first circumferential groove of the bridge bracket by inserting the first coupling protrusion along the first lengthwise groove in the first lengthwise direction and rotating the first coupling protrusion in the first circumferential direction in a state that the first tip bracket of the first tip bracket element is provided inside the first tip cover of the first tip unit and coupled to the first tip cover of the first tip unit and the bridge bracket is provided inside the bridge cover, and the second coupling protrusion of the second tip bracket element is configured to couple with the second circumferential groove of the bridge bracket by inserting the second coupling protrusion along the second lengthwise groove in the second lengthwise direction and rotating the second coupling protrusion in the second circumferential direction in a state that the second tip unit and coupled to the second tip cover of the second tip unit and the bridge bracket is provided inside the bridge cover, wherein the first tip bracket element of the first tip unit is decoupled from the bridge circumferential direction and moving the first coupling protrusion along the first lengthwise groove in the second lengthwise direction in a state that the first tip bracket of the first tip bracket element is provided inside the first tip cover and the first tip unit and coupled to the first tip cover of the first tip unit and the bridge bracket is provided inside the bridge cover, wherein the second tip bracket element of the second tip unit is decoupled from the bridge bracket inside the bridge cover by rotating the second coupling protrusion in the first circumferential direction and moving the second coupling protrusion along the second lengthwise groove in the first lengthwise direction in a state that the second tip bracket of the second tip bracket element is provided inside the second tip cover of the second tip unit and coupled to the second tip cover of the second tip unit and the bridge bracket is provided inside the bridge cover, wherein the bridge bracket, at least a part of the first tip fixing step of the first tip bracket element, and at least a part of the second tip fixing step of the second tip bracket element are provided inside the bridge cover, and wherein the first tip cover of the first tip unit and the bridge cover are connected to each other at a first portion of the dental treatment instrument and have a same external diameter at the first portion of the dental treatment instrument, and the second tip cover of the second tip unit and the bridge cover are connected to each other at a second portion of the dental treatment instrument and have a same external diameter at the second portion of the dental treatment instrument.

2. The dental treatment instrument of claim 1, wherein the first tip unit includes the first tip in a first shape and the second tip unit includes the second tip in a second shape different from the first shape.

3. The dental treatment instrument of claim 1, further comprising an O-ring provided between the bridge unit and the first tip unit and configured to seal a space between the bridge unit and the first tip unit.

4. A dental treatment instrument comprising:

a first tip unit including a first tip in a first shape, a first tip cover and a first tip bracket element coupled to the first tip cover, wherein the first tip cover is configured to support the first tip and the first tip bracket element is detachable from the first tip cover;

a bridge unit configured to be gripped by a user; and a second tip unit including a second tip in a second shape, a second tip cover and a second tip bracket element coupled to the second tip cover, wherein the second tip cover is configured to support the second tip and the second tip bracket element is detachable from the second tip cover, wherein the second shape is different from the first shape, wherein the bridge unit includes a bridge cover in a shape of a hollow cylinder and a bridge bracket inside the bridge cover, wherein the bridge cover includes a first end and a second end and extends from the first end to the second end, wherein the bridge bracket is in a shape of a hollow cylinder having an inner circumferential surface and an outer circumferential surface, includes a first end and a second end and extends from the first end of the bridge bracket to the second end of the bridge bracket, where a length of the bridge cover from the first end of the bridge cover to the second end of the bridge cover is greater than a length of the bridge bracket from the first end of the bridge bracket to the second end of the bridge bracket, wherein the bridge bracket includes:

a first lengthwise groove formed along a first lengthwise direction of the bridge bracket from the first end of the bridge bracket toward the second end of the bridge bracket, a first circumferential groove extending from the first lengthwise groove and formed along a first circumferential direction of the bridge bracket, a second lengthwise groove formed along a second lengthwise direction of the bridge bracket from the second end of the bridge bracket toward the first end of the bridge bracket, the first lengthwise direction being opposite to the second lengthwise direction, and a second circumferential groove extending from the second lengthwise groove and formed along a second circumferential direction of the bridge bracket different from the first circumferential direction, wherein each of the first lengthwise groove, the first circumferential groove, the second lengthwise groove, and the second circumferential groove is a groove passing through from a portion of the inner circumferential surface to a portion of the outer circumferential surface, wherein the first tip bracket element of the first tip unit includes a first tip bracket, a first tip fixing step and a first coupling end portion, and the first tip bracket extends in the second lengthwise direction from the first tip fixing step, and the first coupling end portion extends in the first lengthwise direction from the first tip fixing step and is in a shape of a cylinder having a first outer circumferential surface, and a dimeter of the first tip fixing step is larger than each of a diameter of the first tip bracket and a dimeter of the first coupling end portion, wherein the second tip bracket element of the second tip unit includes a second tip bracket, a second tip fixing step and a second coupling end portion, and the second tip bracket extends in the first lengthwise direction from the second tip fixing step, and the second coupling end portion extends in the second lengthwise direction from the second tip fixing step and is in a shape of a cylinder having a second outer circumferential surface, and a dimeter of the second tip fixing step is larger than each of a diameter of the second tip bracket and a dimeter of the second coupling end portion, wherein the first tip bracket of the first tip bracket element is provided inside the first tip cover of the first tip unit and coupled to the first tip cover of the first tip unit, and the second tip bracket of the second tip bracket element is provided inside the second tip cover of the second tip unit and coupled to the second tip cover of the second tip unit, wherein the first tip bracket element further includes a first coupling protrusion protruding from the first outer circumferential surface of the first coupling end portion in a radial direction vertical to the first lengthwise direction of the bridge bracket, and the second tip bracket element further includes a second coupling protrusion protruding from the second outer circumferential surface of the second coupling end portion in a radial direction vertical to the second lengthwise direction of the bridge bracket, and wherein the first coupling protrusion of the first tip bracket element is configured to couple with the first circumferential groove of the bridge bracket in a state that the first bracket of the first tip bracket element is provided inside the first tip cover of the first tip unit and coupled to the first tip cover of the first tip unit and the bridge bracket is provided inside the bridge cover, and the second coupling protrusion of the second tip bracket element is configured to couple with the second circumferential groove of the bridge bracket in a state that the first tip tip bracket of the second tip bracket element is provided inside the second tip cover of the second tip unit and coupled to the second tip cover of the second tip unit and the bridge bracket is provided inside the bridge cover, wherein the first do bracket element of the first do unit is decoupled from the bridge bracket inside the bridge cover by rotating the first coupling protrusion in the second circumferential direction and moving the first coupling protrusion along the first lengthwise groove in the second lengthwise direction in a state that the first tip bracket of the first tip bracket element is provided inside the first tip cover of the first tip unit and coupled to the first tip cover of the first tip unit and the bridge bracket is provided inside the bridge cover, wherein the second tip bracket element of the second tip unit is decoupled from the bridge bracket inside the bridge cover by rotating the second coupling protrusion in the first circumferential direction and moving the second coupling protrusion along the second lengthwise groove in the first lengthwise direction in a state that the second tip bracket of the second tip bracket element is provided inside the second tip cover of the second tip unit and coupled to the second tip cover of the second tip unit and the bridge bracket is provided inside the bridge cover, wherein the bridge bracket, at least a part of the first tip fixing step of the first tip bracket element, and at least a part of the second tip fixing step of the second tip bracket element are provided inside the bridge cover, and wherein the first tip cover of the first tip unit and the bridge cover are connected to each other at a first portion of the dental treatment instrument and have a same external diameter at the first portion of the dental treatment instrument, and the second tip cover of the second tip unit and the bridge cover are connected to each other at a second portion of the dental treatment instrument and have a same external diameter at the second portion of the dental treatment instrument.

5. The dental treatment instrument of claim 4, further comprising an O-ring provided between the bridge unit and the first tip unit and configured to seal a space between the bridge unit and the first tip unit.

* * * * *